US007078480B2

(12) United States Patent
Nagel et al.

(10) Patent No.: US 7,078,480 B2
(45) Date of Patent: *Jul. 18, 2006

(54) PROCESS FOR STABILIZING THE CONTENT OF GLYCATED PROTEIN OF A SAMPLE ON A MATRIX MATERIAL

(75) Inventors: Rolf Nagel, Bürstadt (DE); Jürgen Mistele, Neulussheim (DE)

(73) Assignee: Roche Diagnostics GmbH (DE)

( * ) Notice: Subject to any disclaimer, the term of this patent is extended or adjusted under 35 U.S.C. 154(b) by 463 days.

This patent is subject to a terminal disclaimer.

(21) Appl. No.: 10/402,757

(22) Filed: Mar. 28, 2003

(65) Prior Publication Data

US 2003/0199079 A1 Oct. 23, 2003

Related U.S. Application Data

(60) Division of application No. 09/316,867, filed on May 21, 1999, now Pat. No. 6,552,165, which is a continuation of application No. 08/702,972, filed on Aug. 26, 1996, now Pat. No. 5,959,076.

(30) Foreign Application Priority Data

Aug. 24, 1995 (DE) ................................ 195 31 173

(51) Int. Cl.
*A61K 38/02* (2006.01)
*B01D 71/00* (2006.01)

(52) U.S. Cl. .......................... 530/322; 530/350; 514/2; 514/8; 427/57; 206/204

(58) Field of Classification Search ..................... None
See application file for complete search history.

(56) References Cited

U.S. PATENT DOCUMENTS 4,107,162 A * 8/1978 Suzuki et al. ............... 544/313
4,216,234 A * 8/1980 Rawlings et al. .............. 426/2
4,334,879 A * 6/1982 Fujimori ...................... 23/230
4,385,632 A * 5/1983 Odelhog ..................... 604/360
4,877,830 A * 10/1989 Dobeli et al. .............. 525/54.3
5,194,333 A * 3/1993 Ohnaka et al. ............. 428/405
5,783,759 A * 7/1998 Wielinger et al. ....... 73/864.72
5,959,076 A * 9/1999 Nagel et al. ................ 530/322
6,231,815 B1 * 5/2001 Bainczyk et al. ........... 422/102
6,552,165 B1 * 4/2003 Nagel et al. ................ 530/322

OTHER PUBLICATIONS

Sazli et al. 'Collection and Storage of Capillary Blood in Glass Fibre Filters for Glycated Haemogobin Measurement by a Microclaorimeteric Method', Ann. Clin. Biochem. vol. 28, pp. 613-617, 1991.*
Iuchi et al. 'A New Method for the Examination of Melituria Spearation and Idenfication of Urinary Sugars by Means of Paper Electorphoresis at High Poetntial Gradient.' Clinica Chimica Acta. vol. 5, No. 1, pp. 42-47. 1960.*
File Caplus on STN, DN No. 109:145535. Okumiiya et al. "Highly sensitive analysis of guanidino compounds using linear gradient elution HPLC" Rinsho Byori (1988), 36(3), 313-317. Abstract Only.*

* cited by examiner

*Primary Examiner*—Anish Gupta
(74) *Attorney, Agent, or Firm*—Woodard, Emhardt, Moriarty, McNett & Henry LLP

(57) ABSTRACT

The invention concerns a method for stabilizing the content of glycated protein in a sample on a matrix material, which is characterized in that the matrix material is impregnated with boric acid buffer with a pH which is larger or equal to 10.5 or a transition metal salt as well as an appropriate matrix material, an element for collecting, transporting and storing sample material to be analysed with such a matrix material and a system containing such an element and a sealable covering.

21 Claims, 1 Drawing Sheet

Figure 1:
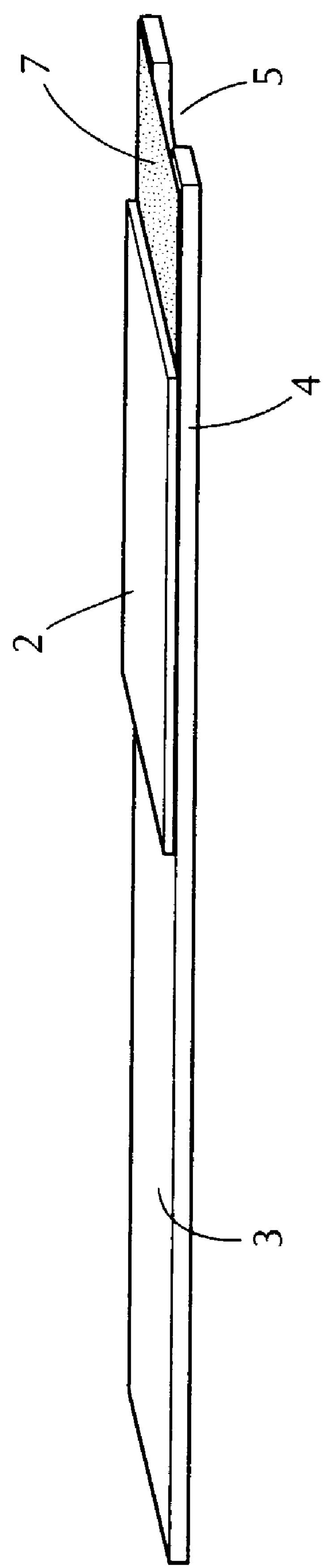

PROCESS FOR STABILIZING THE CONTENT OF GLYCATED PROTEIN OF A SAMPLE ON A MATRIX MATERIAL

REFERENCE TO RELATED APPLICATIONS

This application is a Divisional application claiming priority to U.S. patent application Ser. No. 09/316,867 filed May 21, 1999, now U.S. Pat. No. 6,552,165 which is a Continuation of U.S. patent application Ser. No. 08/702,972, now U.S. Pat. No. 5,959,076 filed Aug. 26, 1996 and to DE 19531173 filed Aug. 24, 1995, which are all incorporated by reference herein in their entirety.

The invention concerns a process for stabilizing the content of glycated protein of a sample on a matrix material and an appropriately treated matrix material for this. In addition the invention concerns an element for collecting, transporting and storing sample material to be analysed containing an absorptive matrix material and a system containing such an element and a sealable covering in which the element can be transported.

The glycation of haemoglobin and serum proteins is increased in patients with diabetes mellitus. The increase is dependent on the glucose concentration and the incubation period of protein with glucose. In these cases the serum proteins, including haemoglobin, are not glycated enzymatically but rather by means of an uncatalysed chemical reaction of glucose with amino groups of proteins. Experts assume that the concentration of a particular protein-glucose adduct reflects the glucose concentration over a particular period as well as the turn-over rate of the protein. Glycated haemoglobin is regarded as an indicator of the average blood glucose concentration during the last two to three months before the blood collection and examination. Glycated serum protein shows the blood glucose concentration during a shorter period of time. The determination of glycated protein such as glycated haemoglobin ($HbA_{1c}$) or glycated serum protein is therefore considerably important for the long-term glycemic control of diabetes patients.

In order to examine blood for the content of glycated protein the sample must often be transported to a far distant laboratory. The content of glycated protein in the sample should not change during this transport period and during a possible subsequent waiting period. The examination of blood samples which had been stored for a long period for glycated haemoglobin is reported in Clinical Chemistry 29, 1080–1082 (1983). This shows that whole blood can be stored up to 21 days at room temperature with essentially no change in the $HbA_{1c}$ content.

However, the transport of liquid blood samples is complicated and involves risks such as breakage of the transport vessel. In addition the puncture of a vein is necessary to collect whole blood although the amounts obtained by withdrawing capillary blood from the finger pad would be sufficient for the analysis. Thus methods have been developed for the transport and analysis of smaller amounts of blood in which capillary blood is applied to filter paper and allowed to dry there. The filter paper is subsequently transported to the site of the examination. Here a disk containing the sample is cut out from the filter paper, eluted and the eluate is examined. The report in Clinical Chemistry 28, 386–387 (1982) refers to such a method. In this report it is stated that the content of glycated protein changes considerably compared to the original sample during blood sample storage on filter paper. After storage of whole blood on filter paper considerably increased measured values for glycated protein are found.

The impregnation of filter paper with glucose oxidase to prevent the increase in the content of glycated haemoglobin caused by storage of blood on filter paper is described in Clinical Chemistry 32, 869–871 (1986). However, impregnation with glucose oxidase was not able to completely prevent the increase of glycated protein. The false increase in the values can only be reduced by this measure. A further disadvantage of impregnating with glucose oxidase is its own instability during storage under the usual storage conditions.

Similar conclusions are reached by an article in Diabetes Care 10, 352–355 (1987). Here it is reported that the treatment of filter paper with glucose oxidase or with ethanol cannot satisfactorily prevent a false increase in the values for glycated haemoglobin when blood is stored on filter paper.

The object of the present invention was therefore to stabilize the content of glycated protein in a sample when stored on a matrix material. After storage of the glycated protein on a matrix material a value should be found for the glycated protein which corresponds to that found after sample collection and before storage.

This object is achieved by the subject matter characterized in more detail in the patent claims.

The invention concerns a process for stabilizing the content of glycated protein of a sample on a matrix material by impregnating the matrix material with a boric acid buffer with a pH greater than or equal to 10.5. A comparable stabilization is also possible when the matrix material carries a transition metal salt.

The invention in addition concerns the matrix material for taking up the sample material which is to be examined for its content of glycated protein which is characterized in that it is impregnated with boric acid buffer with a pH larger than or equal to 10.5 or it carries a transition metal salt.

An additional subject matter of the invention is an element for collecting, transporting and storing sample material to be analysed containing an absorptive matrix material wherein the element is characterized in that the matrix material is impregnated with boric acid buffer with a pH larger than or equal to 10.5 or it carries a transition metal salt.

Finally a subject matter of the invention is a system containing an element characterized as above and a sealable covering in which the element can be transported which is characterized in that the element is such as has already been characterized above as being according to the invention.

Within the scope of the present invention matrix materials denote absorptive materials which are capable of absorbing a liquid containing glycated protein. Glycated protein, i.e. protein carrying sugar residues, is mainly located in the blood but also in sample materials derived from blood such as serum or plasma and moreover also in other body fluids such as urine or saliva. Materials which can absorb such sample materials are preferably fibres but can also be in principle non-fibrous. Preferred fibrous absorptive matrix materials are fleeces, fabrics or knitted fabrics. Fleeces are quite especially preferred. The fibrous matrix materials can contain glass, cellulose, polyester fibres and also viscose and polyvinyl alcohol. Fleece materials containing meltable copolyester fibres in addition to glass fibres, polyester fibres, polyamide fibres, cellulose fibres or cellulose derivative fibres as described in the European Patent Application 0 571 941 can also be used advantageously as the matrix material. Non-fibrous materials can for example be membranes.

According to the invention it has turned out that sample material containing glycated protein that is located on a matrix material can be stored very well without any essential change in the content of glycated protein if the matrix material is impregnated with boric acid buffer with a pH of greater than or equal to 10.5 or if the matrix material carries a transition metal salt. In this case the concentration of the boric acid buffer is of secondary importance. Particularly good results are obtained if the boric acid buffer has a pH value of more than or equal to 11. Suitable buffer concentrations are in the range between 300 and 1000 mmol/l, which corresponds to about 18.6–62 g/100 ml.

Transition metal salts have a similarly good stabilizing action such as nickel or copper salts. Nickel salts are particularly preferred. Water-soluble transition metal salts are preferably used according to the invention. Corresponding chlorides are for example well suited. In order to be active according to the invention transition metal salt concentrations on the matrix material of more than 5 $g/m^2$ and particularly preferably of more than 10 $g/m^2$ have proven to be suitable according to the invention.

Sample material containing glycated protein such as for example glycated haemoglobin which has been applied to a matrix material as described above has resulted in values for glycated protein that are comparable with the original concentration even when measured after a long period of storage at increased temperature. All liquids come into consideration as the sample material which have already been mentioned above. Blood or samples derived from blood such as plasma or serum are quite especially preferred. However, according to the invention in principle all liquids can be used that can contain glycated proteins.

In addition all proteins come basically into consideration as glycated proteins which are formed by chemical reaction of a protein with glucose. Glycated haemoglobin which is also named $HbA_{1c}$ is of particular importance. Glycated albumin or glycated serum proteins should also be mentioned in this connection.

A matrix material as described above which can be used according to the invention to stabilize the content of glycated protein of a sample can also be contained in an element for collecting, transporting and storing sample material to be analysed. Such an element can for example be made like the $HbA_{1c}$ Via Post® sold by Boehringer Mannheim. This element is described in Klin. Lab. 39, 1080–1082 (1993). Instead of a round unimpregnated section of filter paper which is attached to a carrier material, a treated matrix material according to the invention as described above can be used onto which the liquid sample material and in particular blood can be applied in such a way that it is absorbed by the matrix material. In this way the element can be transported to the examination site where the sample is eluted . from the matrix material and the eluate can be examined. By using the matrix material according to the invention the sample material contained therein can be stored for a long period without major changes in the content of glycated protein. The application of the matrix material according to the invention has proven to be particularly suitable in particular for the interesting parameter $HbA_{1c}$.

An element has proven to be particularly suitable for application of the present invention which contains a first and a second layer of absorptive matrix material which are arranged next to and touching one another on an inert carrier material in a contact that enables transfer of liquid in such a way that liquid can pass from the first into the second layer when the first layer is filled with liquid and the first layer can be completely separated from the second layer after application and drying of the sample material. Such an element is described in the German Patent Application P 19 523 061.2. According to the invention a matrix material is used for the first layer which is impregnated as described above and either carries a boric acid buffer with a pH larger than or equal to 10.5 or a transition metal salt.

An important property of the absorptive matrix materials that can be used in such an element is their absorptivity. The absorptivity of the matrix material of the first layer should be equal to or larger than that of the neighbouring layer. This avoids interfering suction effects from developing when sample material is applied to the first layer.

The absorptivity can be determined according to DIN 53106. For this purpose the lower end of samples of 200+/−1 mm in length and 15+/−0.1 mm in width are immersed perpendicularly 25 mm into distilled water and the distance which the water migrates within 10 min is measured in mm. A person skilled in the art knows how different absorptivities can be adjusted in matrix materials with the same components. For example when manufacturing fleeces different thicknesses can be used. The thicker the fibres used the lower is the absorptivity. A further method is to vary the density of fleeces. The absorptivity is reduced by an increase in density.

When using fabrics, fabrics with finer fibres have a higher absorptivity than fabrics with coarser fibres. However, the absorptivity can also be controlled by different types of twisting of the threads. In addition variations in the absorptivity can be achieved via the type of weaving. Further possibilities for varying the absorptivity can be achieved by using different mixtures of fibres. Thus for example the absorptivity is reduced by the addition of hydrophobic fibres.

Stiff materials come into particular consideration as the inert support material on which the matrix material layers are located such as for example plastic foil, cardboard, coated paper etc. The matrix material layers are attached to the inert support material in such a way that the uptake of liquid by the matrix materials is not impaired. This can be achieved by using a double-sided adhesive tape or for example also by using hot-melt adhesive.

The matrix material layers must be attached to the inert support material in such a way that the first layer can be completely separated from the second layer after applying and drying the liquid sample material. This is then in particular possible when the first layer is attached only relatively loosely or at certain points only.

The two matrix material layers must be located on the support material next to and touching one another in such a way that liquid can pass from the first layer into the second layer when the first layer is filled with liquid. This is then possible when at least the edges of the two layers are touching. It is even better, however, if there is a slight overlap of the two layers. It is particularly preferred that the layers are arranged such that the second layer slightly overlaps the first layer.

The size of the matrix material layers must be selected such that the first layer, which is later also to be used as the analytical layer, can be completely filled with the sample liquid. Excess sample liquid is then taken up by the second layer. The amount of sample which is adequate to determine a particular analyte depends on the type of analyte to be determined. However, as a rule 5–20 μl and usually 10 μl sample is adequate. This volume must be taken up by the first matrix layer and capable of being eluted again later. For safety reasons the second matrix layer which has the function of a suction layer should be able to absorb a larger volume. Suction volumes of 10–50 μl, preferably 10–30 μl particularly preferably 20 μl are usually adequate for this purpose. It is expedient that the usual dimensions of the matrix material layers are such that the suction volume of the two matrix material layers taken together is at least 30 µl and preferably at least 50 µl. Such a dimension ensures that the same amount of sample is applied on the first matrix layer of various elements according to the invention with small as well as with large drops of liquid. In order to achieve an adequate suction volume the smaller first layer usually has an area of 3×3 to 8×8 mm.

The arrangement of matrix material layers described above enables a homogeneous distribution of liquid sample material to be achieved in the first layer. Due to the fact that the first layer is completely filled with liquid sample material, reproducible amounts always reach the analysis after separation and elution of the first layer.

In order to transport an element according to the invention after applying the sample material to the analytical station it has also proven to be expedient to transport it in a sealable covering. The covering and element thus form a system. An envelope is for example suitable as the sealable covering such as a letter envelope which encompasses a front part and two side parts as well as a backflap and a sealing flap with which the envelope can for example be glued. Such a covering is also described in the German Patent Application P 19 523 061.2.

The invention is elucidated further in the following examples.

EXAMPLE 1

Stabilizing $HbA_{1c}$ by Boric Acid Buffer

A first layer (1) of an absorptive matrix material is fixed with the aid of a double-sided adhesive tape (4) to a polyester support foil (3) of dimensions 49×6 mm with a semicircular punch hole (5) of 5 mm at its short-sided end as shown in FIG. 1 in such a way that 0.5 to 1 mm of its width is glued onto the adhesive tape (4). The later detachability is positively influenced by this relatively narrow attachment. The second layer (2) of the absorptive matrix material is glued in a width of 5 mm or more.

A fleece which has been manufactured on a paper machine which has the following data is used for the first layer of absorptive matrix material:

80 parts polyester fibres (fibre diameter 1.7 Dtex), 20 parts viscose, 20 parts polyvinyl alcohol; area weight 80 g/m$^2$; suction height 102 mm (DIN 53106).

This fleece was impregnated with one of the boric acid buffers listed in table 1 (62 g boric acid suspended in 800 ml distilled water, adjusted to the desired pH value with 5 mol/l potassium hydroxide solution and filled up to 1000 ml with distilled water), dried at 50° C. and subsequently cut to a size of 6×6 mm. This matrix takes up ca. 10 µl of liquid.

A fleece is used for the second layer of absorptive matrix material which corresponds to the first layer but is not impregnated with boric acid buffer.

Ca. 10 µl EDTA blood containing 5.1 % $HbA_{1c}$ supplemented with 500 mg/dl glucose is applied in each case to the elements according to the invention manufactured in this manner and dried at room temperature for at least 2 hours, In order to simulate a transport the dried sample carriers were stressed for 5 days at 35° C. in shipping envelopes.

After removing the first matrix layer with tweezers, the matrix material is eluted in 1 ml haemolysis reagent for the Tina-quant® test of Boehringer Mannheim GmbH (Germany) (order number 1 488 457). Subsequently $HbA_{1c}$ is determined according to the immunological method of determination of Boehringer Mannheim GmbH (Germany) on a Hitachi 717 instrument from Boehringer Manriheim GmbH using reagent with order number 1 488 414 from Boehringer Mannheim GmbH.

The measured results are summarized in table 1 for elements in which the matrix material contains no boric acid buffer or boric acid buffer of various pH values.

TABLE 1

| | Storage conditions 5 days at | |
|---|---|---|
| Matrix impregnated with | 2 to 8° C. $HbA_{1c}$(%) | 35° C. $HbA_{1c}$(%) |
| without boric acid | 5.6 | 11.2 |
| boric acid pH 6.3 | 5.3 | 10.6 |
| boric acid pH 7.0 | 5.4 | 10.1 |
| boric acid pH 8.0 | 5.3 | 9.1 |
| boric acid pH 9.0 | 5.2 | 7.9 |
| boric acid pH 10.0 | 5.5 | 7.0 |
| boric acid pH 10.5 | 5.0 | 6.0 |
| boric acid pH 11.0 | 5.2 | 5.5 |
| boric acid pH 12.0 | 5.1 | 5.3 |

The result shows that boric acid buffer above a pH value of 10.5 leads to a stabilization of the non-enzymatically glycosylated protein to such an extent that after temperature stress adequate unchanged concentration values are present.

EXAMPLE 2

Stabilization of $HbA_{1c}$ by Nickel(II)Chloride

Analogously to example 1 elements for collecting, transporting and storing sample material to be analysed are manufactured in which, however, the first matrix layer has been impregnated with a $NiCl_2$ concentration series between 0 and 200 mmol/1 $NiCl_2$ (0; 9.6; 14.4; 19.2; 24.0 and 48 g/l nickel chloride-6 hydrate dissolved in 1000 ml distilled water) in such a way that various nickel salt concentrations are present in the matrix as listed in table 2. A blood sample such as the one used in example 1 containing 5.1 % $HbA_{1c}$ supplemented with 500 mg/dl glucose was used. Determination of $HbA_{1c}$ as in example 1 resulted in the concentration values listed in table 2.

TABLE 2

| | Storage conditions 5 days at | |
|---|---|---|
| Matrix impregnated with $NiCl_2$(g/m$^2$) | 2 to 8° C. $HbA_{1c}$(%) | 35° C. $HbA_{1c}$(%) |
| 0 | 5.6 | 11.2 |
| 4.2 | 5.4 | 8.2 |
| 6.3 | 5.1 | 6.3 |
| 8.4 | 5.2 | 5.7 |
| 10.5 | 4.9 | 5.8 |
| 21.0 | 5.3 | 4.9 |

The invention claimed is:

1. An element for collecting, transporting or storing a sample to be analyzed, said element comprises an absorptive matrix material, wherein the matrix material is a fibrous material carrying a water soluble, non-ionically bound transition metal salt which dissolves off of said matrix material by an aqueous solution, and wherein the element contains a first layer and a second layer of absorptive material, said first and second layers positioned on an inert carrier and in contact with each other to enable transfer of a liquid in such a way that the liquid can pass from the first layer into the second layer when the first layer is filled with the liquid and wherein the first layer can be completely separated from the second layer after application and drying of the sample.

2. The element of claim 1 wherein the first layer carries the water soluble, non-ionically bound transition metal salt which dissolves off of said matrix material by an aqueous solution.

3. The element of claim 1 wherein the transition metal salt is a nickel salt or a copper salt.

4. An element for collecting a liquid sample containing a glycated protein, said element comprising:

a first layer impregnated with a dried boric acid and buffer combination selected to maintain a solution at a pH of at least 10.5 when solubilized or a transition metal salt; and a second layer positioned on the element in contact with the first layer, said second layer comprising a material selected to have greater absorption of the liquid material than the first layer, wherein the first layer is separable from the second layer.

5. The element of claim 4, wherein the first layer is sized to absorb between about 5 μl and about 20 μl of the liquid sample.

6. The element of claim 4 wherein the first layer is a fibrous matrix.

7. The element of claim 6 wherein the first layer is composed of a material selected from the group consisting of: fleeces, fabrics, knitted fabrics, glass, cellulose, polyester fibers and polyvinyl alcohol.

8. The element of claim 4 wherein the first layer is non-fibrous.

9. The element of claim 4 wherein the first layer is impregnated with a dried boric acid and buffer combination selected to maintain a solution at a pH of at least 11 when solubilized.

10. The element of claim 4 wherein the first layer is impregnated with nickel salt or a copper salt.

11. The element of claim 10 wherein the first layer is impregnated with a water soluble nickel salt.

12. The element of claim 10 wherein the first layer is impregnated with greater than about 5 $g/m^2$ of the nickel salt or the copper salt.

13. The element of claim 4 wherein the first layer is sized to absorb between about 5 μl and about 20 μl.

14. The element of claim 4 wherein the second layer partly overlaps the first layer.

15. The element of claim 4 wherein the second layer is sized to absorb between about 10 μl and about 50 μl.

16. The element of claim 4 comprising an inert carrier positioned underneath the first and second layers and selected from the group consisting of: plastic foil, cardboard, and coated paper.

17. A system for collecting, transporting or storing a sample to be analyzed, said system comprising:

an element comprising a first layer impregnated with a dried boric acid and buffer combination selected to maintain a solution at a pH of at least 10.5 when solubilized or a transition metal salt and a second layer positioned in contact with the first layer, said second layer comprising a material selected to have greater absorption of the liquid material than the first layer, wherein the first layer is separable from the second layer; and, a sealable covering configured to receive the element.

18. The system of claim 17 wherein the sealable covering comprises a sealable envelope.

19. The system of claim 17 wherein the sealable covering is configured to receive the first layer separated from the second layer.

20. The system of claim 17 wherein the element comprises an inert carrier positioned underneath the first and second layers.

21. The system of claim 20 wherein the sealable covering is sized to receive the element.

* * * * *